US011160896B1

(12) United States Patent
Yang (10) Patent No.: US 11,160,896 B1
(45) Date of Patent: Nov. 2, 2021

(54) LIGHT BLOCKING APPARATUS AND AIR PURIFIER

(71) Applicant: SHENZHEN ANTOP TECHNOLOGY CO., LTD, Shenzhen (CN)

(72) Inventor: Ruidian Yang, Shenzhen (CN)

(73) Assignee: SHENZHEN ANTOP TECHNOLOGY CO., LTD, Shenzhen (CN)

( * ) Notice: Subject to any disclaimer, the term of this patent is extended or adjusted under 35 U.S.C. 154(b) by 0 days.

(21) Appl. No.: 17/107,293

(22) Filed: Nov. 30, 2020

(30) Foreign Application Priority Data

Aug. 28, 2020 (CN) .......................... 202021854684.9

(51) Int. Cl.
*A61L 9/20* (2006.01)
(52) U.S. Cl.
CPC ............. *A61L 9/20* (2013.01); *A61L 2209/12* (2013.01)
(58) Field of Classification Search
None
See application file for complete search history.

(56) References Cited

U.S. PATENT DOCUMENTS

| | | | |
|---|---|---|---|
| 10,293,072 B2 * | 5/2019 | Taghipour | A61L 9/205 |
| 10,434,208 B1 * | 10/2019 | Ngo | H05B 47/19 |
| 10,485,946 B2 * | 11/2019 | Reese | A62B 7/10 |
| 10,893,990 B1 * | 1/2021 | Uda | B60H 3/0078 |
| 2006/0018804 A1 * | 1/2006 | Snyder | A61L 9/22 422/121 |
| 2006/0018805 A1 * | 1/2006 | Yuen | A61L 9/22 422/121 |
| 2006/0177356 A1 * | 8/2006 | Miller | A61M 11/06 422/121 |
| 2008/0019861 A1 * | 1/2008 | Silderhuis | F24F 8/192 422/3 |
| 2008/0152548 A1 * | 6/2008 | Clark | A61L 9/205 422/121 |
| 2010/0254852 A1 * | 10/2010 | Metteer | A61L 9/02 422/4 |
| 2013/0183214 A1 * | 7/2013 | Metteer | A61L 9/015 423/210 |
| 2013/0291735 A1 * | 11/2013 | Livchak | F24F 1/01 96/224 |
| 2018/0264157 A1 * | 9/2018 | Benedek | B01D 46/0027 |
| 2019/0099050 A1 * | 4/2019 | Kirschman | A61L 9/20 |
| 2019/0105422 A1 * | 4/2019 | Jeong | F25D 17/04 |
| 2019/0134251 A1 * | 5/2019 | Jeong | A61L 9/20 |
| 2019/0175779 A1 * | 6/2019 | Baek | A61L 9/22 |
| 2019/0240370 A1 * | 8/2019 | Benedek | A61L 9/122 |
| 2019/0240371 A1 * | 8/2019 | Benedek | B01D 46/0028 |
| 2020/0009283 A1 * | 1/2020 | Gardner | A61L 9/046 |
| 2020/0289698 A1 * | 9/2020 | Polidoro | F21V 21/04 |
| 2020/0289985 A1 * | 9/2020 | Drake | A61L 9/20 |

(Continued)

*Primary Examiner* — Andrew Smyth
(74) *Attorney, Agent, or Firm* — Erickson Kernell IP, LLC; Kent R. Erickson (57) ABSTRACT

Provided are a light blocking apparatus and an air purifier including the light blocking apparatus. The light blocking apparatus includes a housing, a light blocking member and a through hole. The through hole is located in the housing. A spacing or a gap is provided between the light blocking member and the housing. Projection of the light blocking member in spaced relationship from the housing covers the through hole.

7 Claims, 8 Drawing Sheets

(56) References Cited

U.S. PATENT DOCUMENTS

| | | | |
|---|---|---|---|
| 2020/0297891 A1* | 9/2020 | Epperson | A61L 9/20 |
| 2020/0405901 A1* | 12/2020 | Saccardo | B01D 53/346 |
| 2021/0010692 A1* | 1/2021 | Worrilow | B01D 53/44 |
| 2021/0052764 A1* | 2/2021 | Terkelsen | F24F 8/192 |

* cited by examiner

Fig.8

LIGHT BLOCKING APPARATUS AND AIR PURIFIER

CROSS-REFERENCE TO RELATED APPLICATIONS

This application is based on and claims the benefit of priority from Chinese Patent Application No. 202021854684.9, filed on 28 Aug. 2020, the entirety of which is incorporated by reference herein.

FIELD OF THE INVENTION

The present disclosure relates to the field of air purification technology, and in particular, to a light blocking apparatus and an air purifier.

BACKGROUND

Ultraviolet light has a sterilizing effect and may be used for air disinfection and purification. However, ultraviolet light is somewhat detrimental to physical health. In the related technologies, a purification apparatus, which uses an ultraviolet lamp for air sterilization and disinfection, includes opening structures such as an air inlet, an air outlet and the like in communication with surroundings, so that ultraviolet light emitted by the ultraviolet lamp may scatter to the outside of the air purification apparatus through the opening structures, posing potential safety hazards.

SUMMARY

The present disclosure aims to at least resolve one of the technical problems in the related technologies. In view of this, the present disclosure provides a light blocking apparatus and an air purifier, which can reduce the probability of scattering ultraviolet light to the surroundings, thus reducing damage to a user.

In an embodiment of the present disclosure, there is provided a light blocking apparatus, including:

a housing provided with a through hole, opening or slot; and a light blocking member, a gap or an angle being provided or formed between the light blocking member and the housing, and projection of the light blocking member toward the housing covering the through hole.

The light blocking apparatus in this embodiment of the present disclosure at least has the following beneficial effects. The projection of the light blocking member toward the housing can cover the through hole, so that when an ultraviolet lamp at a side of the housing emits light, air can pass through the through hole to enter an irradiation zone of the ultraviolet lamp. Meanwhile, because of the blockage by the light blocking member, the probability of scattering the ultraviolet light to the outside surroundings can be reduced, thus reducing damage to a user.

In some embodiments, the light blocking apparatus includes a first connecting member having one end connected to the light blocking member and the other end thereof connected to the housing.

In some embodiments, the light blocking apparatus includes several first connecting members, the housing is provided with several through holes, each of the first connecting members is connected to the light blocking member, and all of the first connecting members are connected to the housing.

In some embodiments, the light blocking apparatus further includes a second connecting member, the light blocking apparatus includes several light blocking members, the housing is provided with several through holes, each light blocking member corresponds to a respective one of the through holes, one end of the second connecting member is connected to all of the light blocking members, and the other end of the second connecting member is connected to the housing.

In some embodiments, a portion of an edge of the light blocking member is connected to the housing.

In some embodiments, the housing includes an accommodating cavity with a cavity wall, the through holes are located in the cavity wall, and the light blocking member is located inside or outside the accommodating cavity.

An embodiment of the present disclosure further provides an air purifier, including the light blocking apparatus described above.

In some embodiments, the air purifier further includes a top housing which is connected to the housing to form a casing of the air purifier.

In some embodiments, the air purifier includes a casing, and the light blocking apparatus is located inside the casing.

An embodiment of the present disclosure further provides an air purifier, including the light blocking apparatus described above, where the air purifier further includes a casing and an ultraviolet lamp, the light blocking apparatus is located inside a housing, and the ultraviolet lamp is located in the accommodating cavity.

Reference numerals: light blocking apparatus 101, housing 102, through hole 103, light blocking member 104, windward side 105, gap 106, second connecting member 401, accommodating cavity 202, first connecting member 201, casing 601, inlet 602, outlet 603, ultraviolet lamp 604, and top housing 801.

DETAILED DESCRIPTION

The conception of the present disclosure and achieved technical effects are clearly and completely described as below with reference to embodiments, so as to fully understand the objectives, features, and effects of the present disclosure. Obviously, the described embodiments are only a part of, not all of, the embodiments of the present disclosure. All other embodiments obtained by a person skilled in the art based on the embodiments of the present disclosure without creative effort shall fall into the protection scope of the present disclosure.

In the description of the embodiments of the present disclosure, if directional descriptions are involved, for example, directional or positional relationships indicated by "up", "down", "front", "back", "left", "right", etc. are based on the directional or positional relationships shown in the accompanying drawings, they are intended only to facilitate the description of the present disclosure and simplify the description, instead of indicating or implying the apparatus or element referred to must have a particular direction and be constructed and operated in the particular direction a, and thus cannot be construed as limitations on the present disclosure.

In the description of the embodiments of the present disclosure, if a feature is referred to as "disposed on", "fixed to", "connected to", or "mounted to" another feature, it may be directly disposed on, fixed to, or connected to the another feature or indirectly disposed on, fixed to, connected to, or mounted to the another feature. In description of the embodiments of the present disclosure, if "several" is involved, it means more than one; if "a plurality of" is involved, it means more than two; if "greater than", "less than", and "more than" are involved, they should all be understood as not including the number; if "above", "below", and "within" are involved, they should all be understood as including the number. If "first" and "second" are involved, they should be understood as being used to distinguish technical features, but not to indicate or imply relative importance or implicitly indicating the number of indicated technical features or a precedence relationship of the indicated technical features.

An ultraviolet lamp is usually used in an air purification device in the related technologies to implement the functions of disinfection and sterilization. However, because the air purification device includes an air inlet, ultraviolet light is prone to leakage through the air inlet, posing potential safety hazards.

Figure 1:
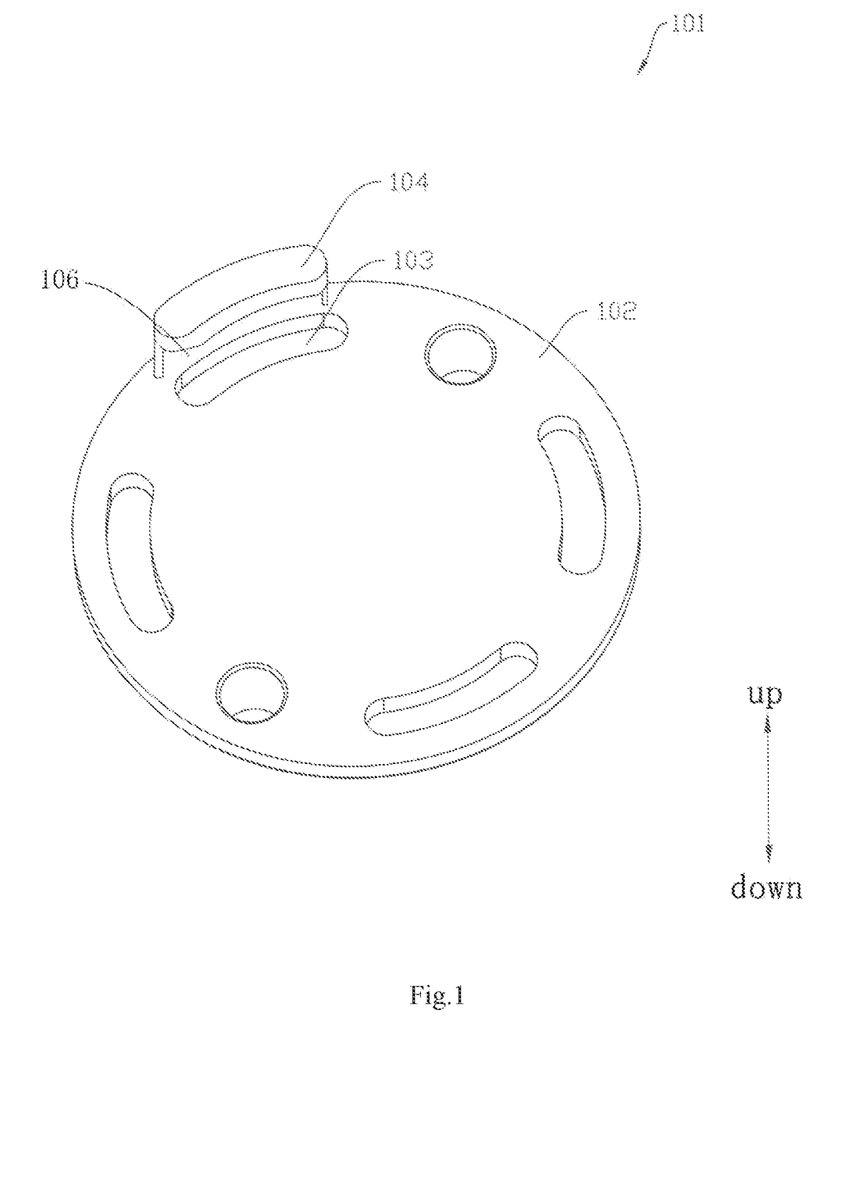
FIG. 1 is a perspective view of a light blocking apparatus according to an embodiment of the present disclosure.

To resolve the foregoing problem, an embodiment of the present disclosure provides a light blocking apparatus 101. As shown in FIG. 1, the light blocking apparatus 101 includes a housing 102 and a light blocking member 104. The housing is provided with a through hole, opening or slot 103. The light blocking member 104 extends in spaced relationship from the housing 102 and covers the through hole 103 with a gap or an angle 106 formed or provided between the light blocking member 104 and the housing 102. Because the gap or angle is provided between the light blocking member 104 and the housing 102, air can pass through the through hole 103 from bottom to top as shown in FIG. 1. Ultraviolet light emitted from an ultraviolet light source located above the housing 102 as shown in FIG. 1 is used to disinfect and sterilize air (in this case, it is assumed that the ultraviolet light source is located above as shown in FIG. 1). Because the light blocking member 104 extending in spaced relationship from the housing 102 covers the through hole 103, the foregoing structure significantly reduces the scattering of the ultraviolet light from the through hole 103 to the outside (from top to bottom as shown in FIG. 1), thereby reducing a probability of potential safety hazards.

Specifically, as shown in FIG. 1, the housing 102 is provided with several through holes. The light blocking apparatus 101 includes the light blocking members 104. Each light blocking member 104 corresponds to one through hole 103. It can be conceived that the housing 102 may be provided with several through holes 103. All the through holes 103 are blocked by one same light blocking member 104. It may be conceived that the housing 102 may be provided with several sets of through holes. Each set includes several through holes 103. The through holes 103 in one set are blocked by one light blocking member 104.

More specifically, as shown in FIG. 1, it is assumed that a source of emitting ultraviolet light is located above as shown in FIG. 1. The light blocking member 104 may be located below the housing 102 or may be located above the housing 102, provided that the light blocking member can block light rays.

In another embodiment, as shown in FIG. 1, the light blocking member 104 may be connected to the housing 102 by a frame body, so that the light blocking member 104 can be better supported.

Figure 2:
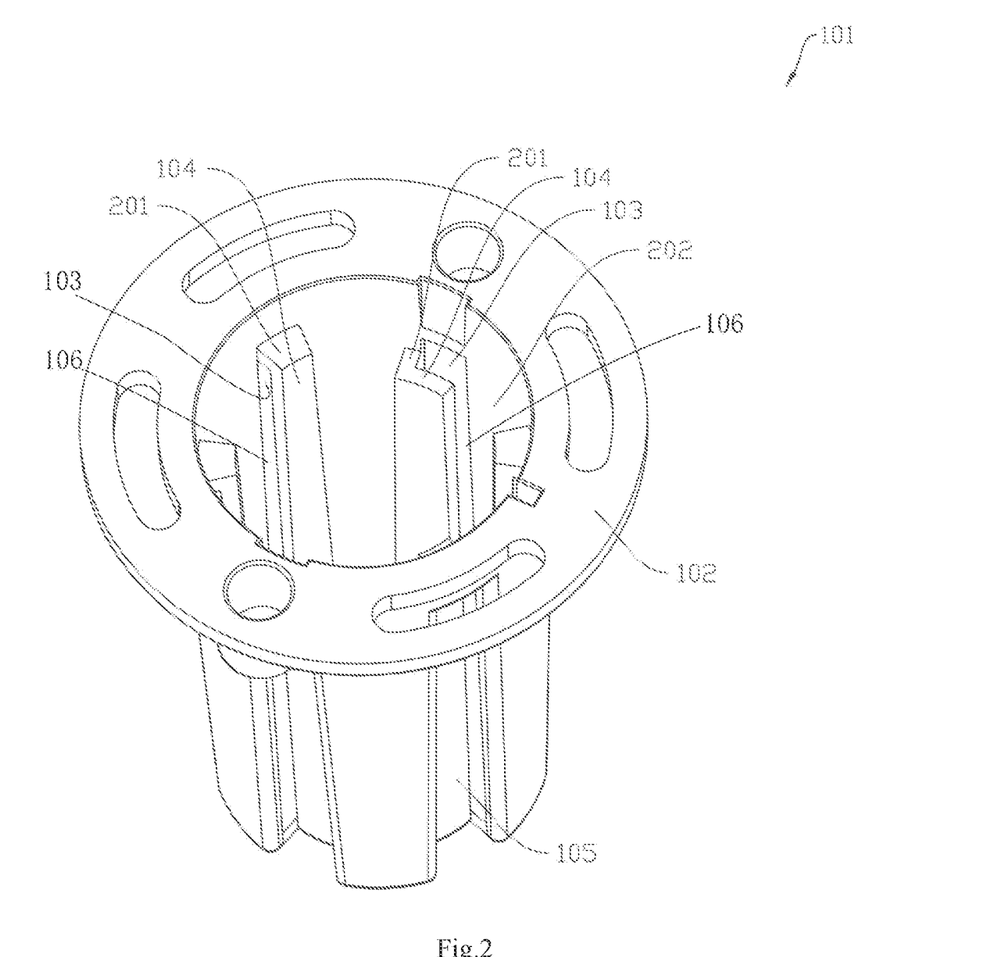
FIG. 2 is a perspective view of a light blocking apparatus according to another embodiment of the present disclosure.
Figure 3:
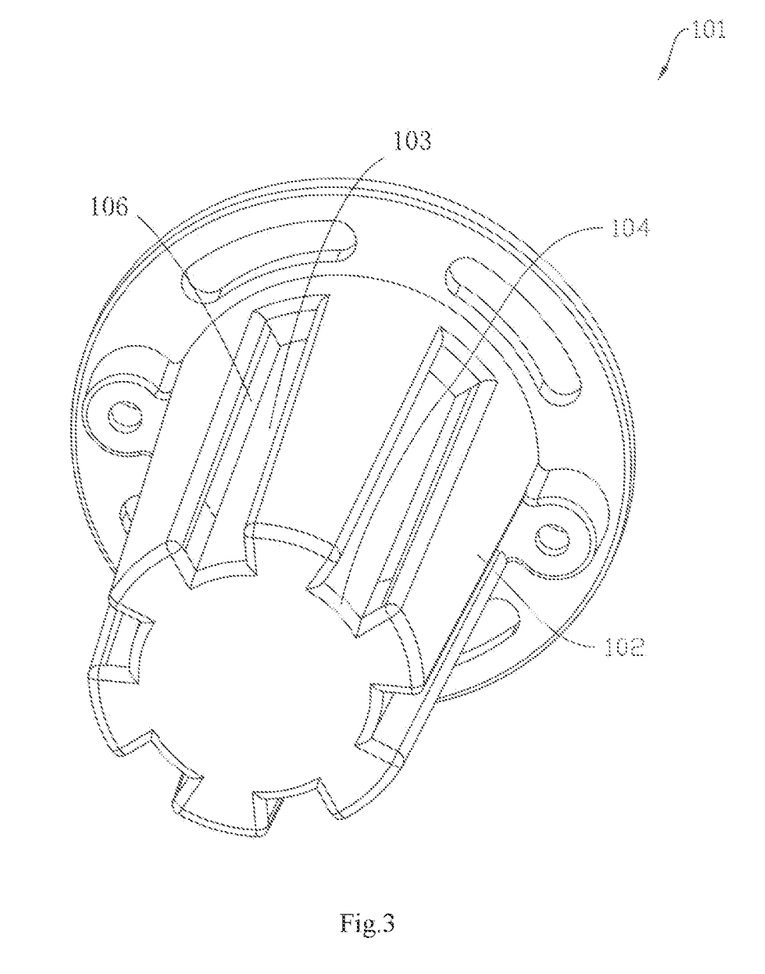
FIG. 3 is a perspective view of the light blocking apparatus of FIG. 2 from another view.

In another embodiment, as shown in FIG. 2 and FIG. 3, a first connecting member 201 is further included. One end of the first connecting member 201 is connected to the light blocking member 104, and the other end of the first connecting member 201 is connected to the housing 102, so that the light blocking member 104 can be supported by the housing 102.

Specifically, as shown in FIG. 2 and FIG. 3, the light blocking member 104 has a rectangular plate-form structure. The first connecting member 201 may be connected to any edge of the light blocking member 104. It can be conceived that the first connecting member 201 may be connected at any position of the light blocking member 104, provided that it provides sufficient support to the light blocking member 104 The light blocking member 104 may alternatively have another shape, for example, a shape of curved plate or a shape of block structure, provided that the light blocking member can block light rays. When the light blocking member 104 is of a structure having an irregular shape, the first connecting member 201 may still be connected at any position of the light blocking member 104, provided that the light blocking member 104 can block light.

Specifically, as shown in FIG. 2, in the foregoing embodiment, a gap 106 is provided between the light blocking member 104 and the base 102. The light blocking member 104 is connected to the base 102 by the first connecting member 201.

Specifically, as shown in FIG. 2, the light blocking member 104 is provided with a windward side 105. The windward side 105 is provided with a boss in a direction from which the wind is blowing. The boss may be U-shaped or V-shaped. The foregoing structure can reduce the wind resistance of the light blocking member 104.

Figure 4:
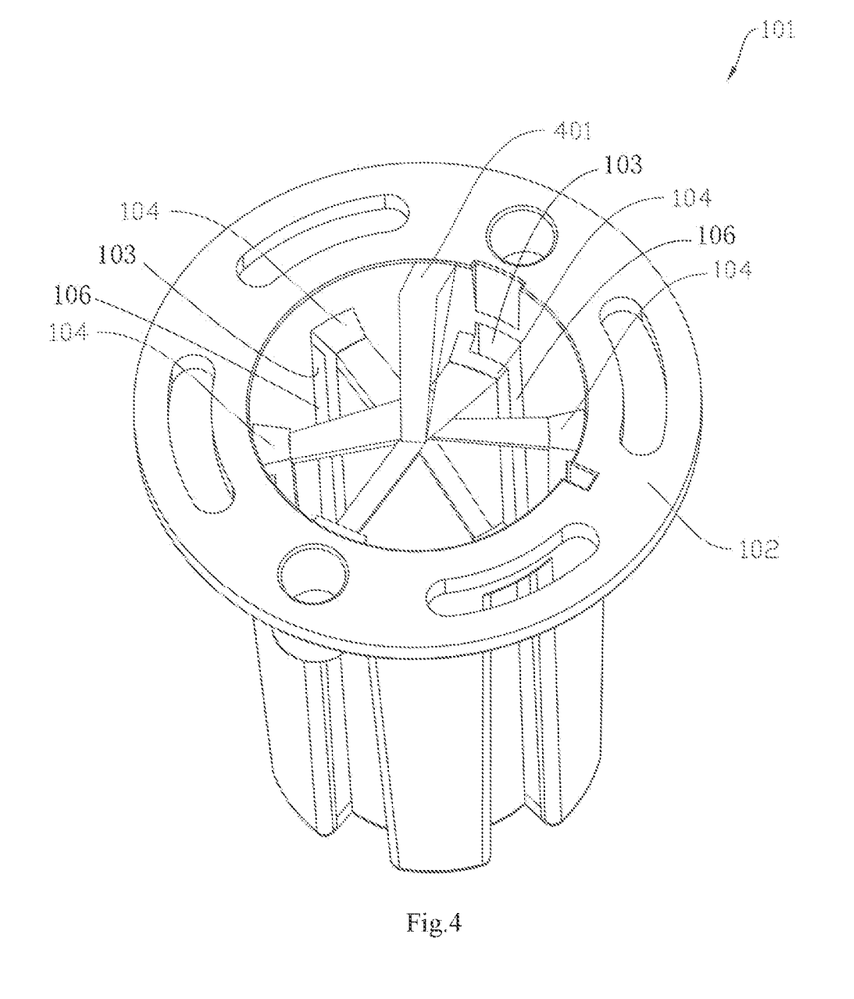
FIG. 4 is a perspective view of a light blocking apparatus according to a third embodiment of the present disclosure.

In another embodiment, as shown in FIG. 4, the light blocking apparatus 101 includes a second connecting member 401 and several through holes 103. Each light blocking member 104 is connected to the same second connecting member 401. The second connecting member 401 may be connected to the housing 102, so that all the light blocking members 104 can be connected to the housing 102 by one connecting member.

Specifically, as shown in FIG. 4, in the foregoing embodiment, a gap 106 is provided between the light blocking member 104 and the housing 102. The light blocking member 104 is connected to the housing 102 by the second connecting member 401.

In the foregoing embodiment, the first connecting member 201 and the second connecting member 401 may be for example embedded into, sap-fitted with, riveted with, or integral with the housing 102.

In another embodiment, the light blocking member 104 may be directly connected to the housing 102. That is, a portion of an edge of the light blocking member 104 is connected to the housing 102, and another portion of the edge of the light blocking member 104 wraps toward the inside or outside of the housing 102, so that the light blocking member 104 can be directly connected to the housing 102 without hindering air from passing through the through hole 103.

It may be understood that in the foregoing embodiment, an angle is provided between the light blocking member 104 and the housing 102.

In the embodiment as shown in FIG. 2, the light blocking apparatus includes an accommodating cavity 202. The accommodating cavity 202 includes a cavity wall. The through holes 103 are located in the cavity wall. When the accommodating cavity 202 has a regular shape, the cavity wall includes a bottom wall and a side wall. As shown in FIG. 3 and FIG. 4, the through holes 103 are located in the side wall of the accommodating cavity 202, and the light blocking member 104 is located in the accommodating cavity 202 at a position corresponding to the through hole 103. Such a structure enables an accommodating space (that is, an interior of the accommodating cavity 202) to be formed by the light blocking apparatus. An ultraviolet light emission source may be placed in the accommodating space, such that air that enters the housing 102 through the through holes 103 are better sterilized and disinfected by ultraviolet light.

It can be conceived that the through holes 103 may be alternatively located in the bottom wall of the accommodating cavity 202.

Figure 5:
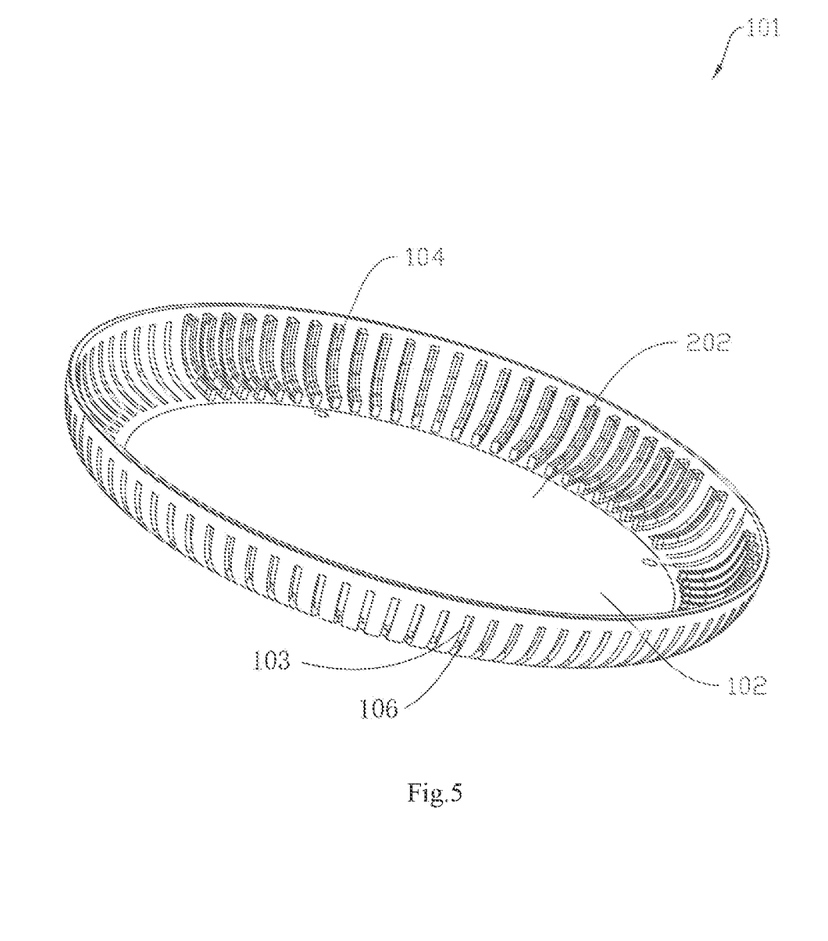
FIG. 5 is a perspective view of a light blocking apparatus according to a fourth embodiment of the present disclosure.

It can be conceived that as shown in FIG. 5, when the accommodating cavity 202 has a curved-surface structure, the through holes 103 may be located in the curved-surface structure. It can further be conceived that when the accommodating cavity 202 has an irregular shape, the through holes 103 may be provided at any position as long as both a circulation requirement of air and a blockage requirement of the light blocking member 104 are met.

It can be conceived that the light blocking member 104 may be alternatively located outside the accommodating cavity 202. That is, the first connecting member 201 connected to the light blocking member 104 protrudes towards the outside of the accommodating cavity 202 and is connected to the accommodating cavity 202.

An embodiment of the present disclosure further provides an air purifier including the light blocking apparatus 101 described in any foregoing embodiment. Because the light blocking apparatus 101 can block ultraviolet light, the probability of potential safety hazards can be reduced during the use of the air purifier adopting the foregoing light blocking apparatus 101.

Figure 6:
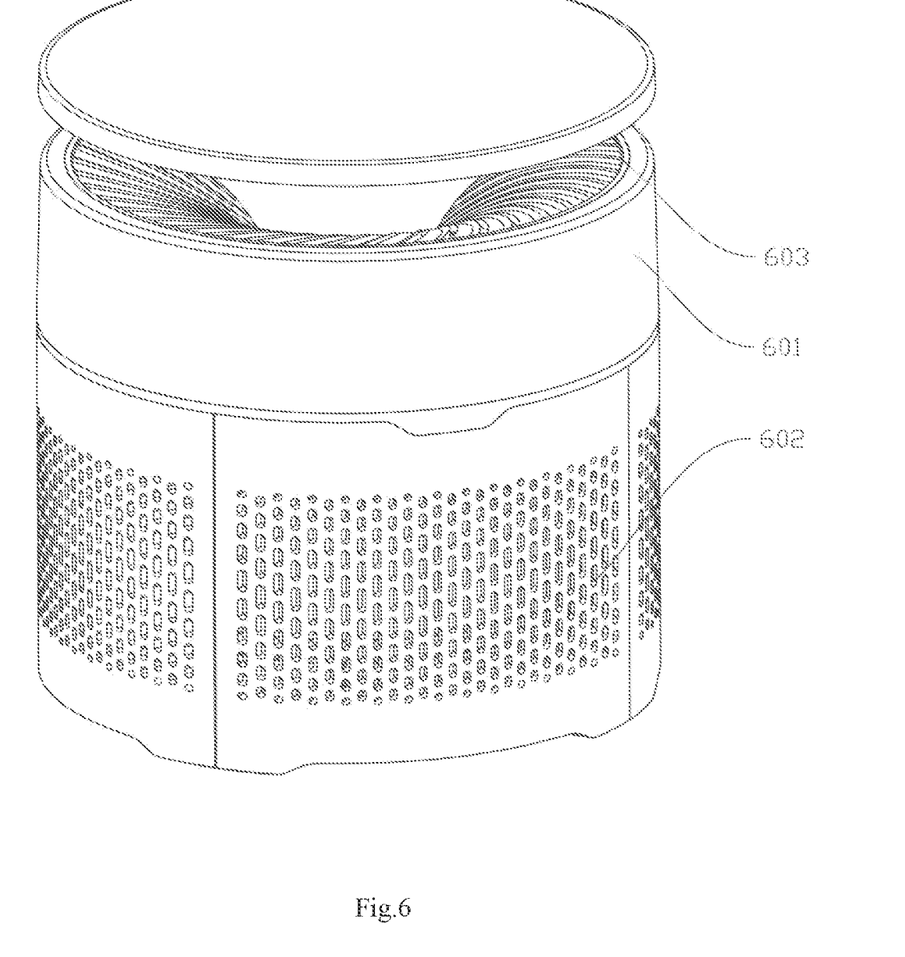
FIG. 6 is a perspective view of an air purifier according to an embodiment of the present disclosure.
Figure 7:
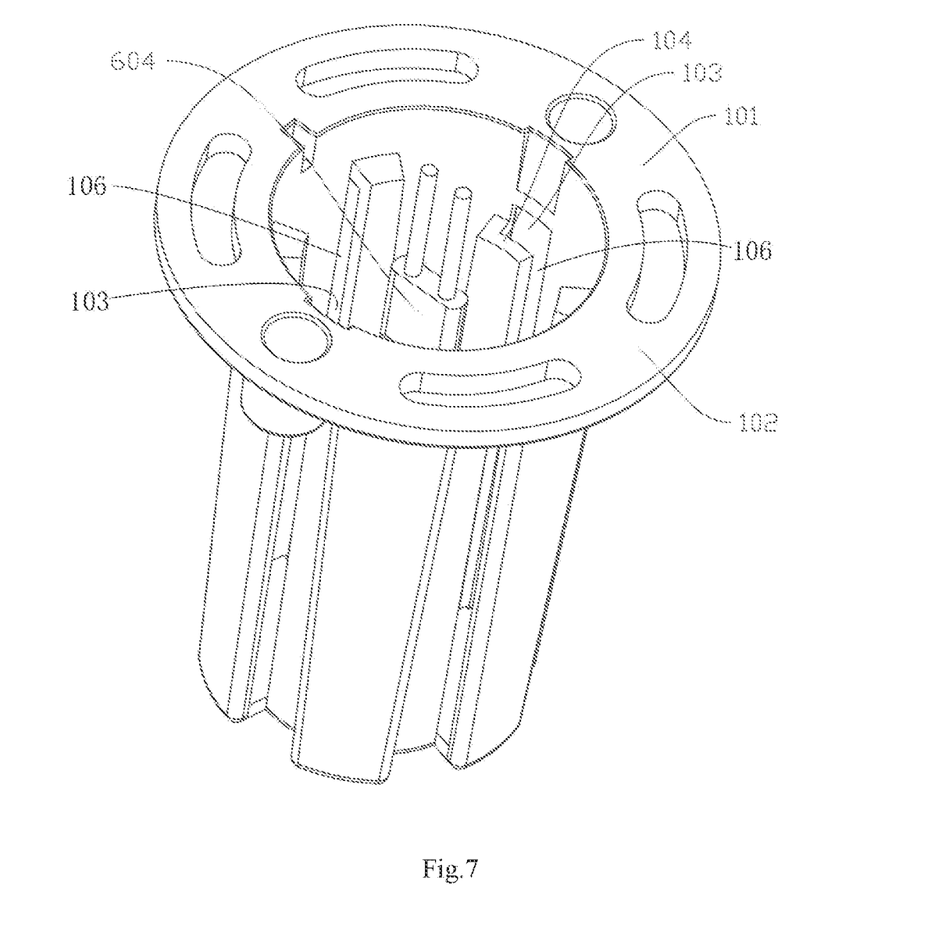
FIG. 7 is a perspective view of a partial structure in FIG. 6.

In another embodiment, as shown in FIG. 6 and FIG. 7, the air purifier includes a casing 601 and an ultraviolet lamp 604. The casing 601 is provided with an inlet 602 and an outlet 603. The light blocking apparatus 101 is located inside the casing 601. The light blocking apparatus 101 can cover ultraviolet light emitted by the ultraviolet lamp 604, to reduce the probability of leakage of ultraviolet light. In this embodiment of the present disclosure, during the use of the air purifier, air that enters the air purifier through the inlet 602 and passes through the through holes 103 to reach the range of an irradiation area of the ultraviolet lamp 604 is sterilized and disinfected by ultraviolet light, and then passes through the outlet 603 to flow out of the air purifier. Because the projection of the light blocking member 104 toward the housing 102 covers the through hole 103, the light blocking member 104 can block ultraviolet light irradiated toward the through hole 103, to effectively reduce the leakage of ultraviolet light, so that the potential safety hazards of the air purifier can be reduced.

Specifically, as shown in FIG. 7, the ultraviolet lamp 604 of the air purifier is located inside the accommodating cavity 202 of the housing 102, so that a space occupied by the ultraviolet lamp 604 can be effectively reduced.

More specifically, the air purifier further includes a third connecting member. The ultraviolet lamp 604 is connected to the housing 102 by the third connecting member. The third connecting member is a frame body structure provided with several relatively large gaps. The gaps may enable air entering the accommodating cavity 202 through the through hole 103 to be sterilized and disinfected by the ultraviolet lamp 604 before smoothly flowing out of the accommodating cavity 202, and then out of the air purifier through the outlet 603.

Figure 8:
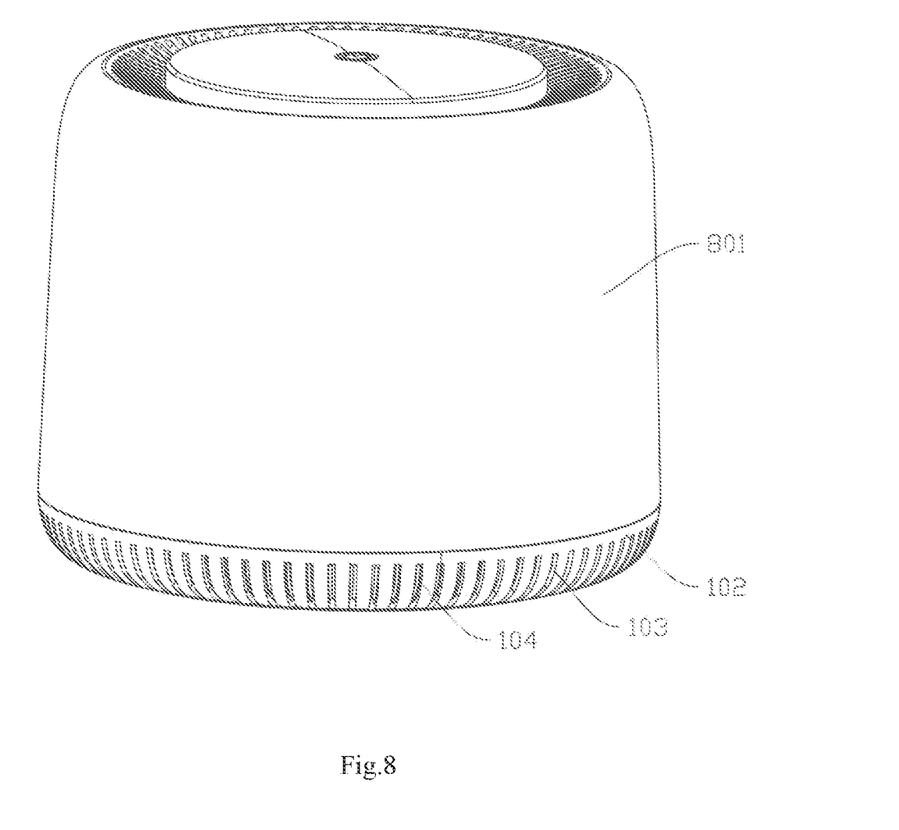
FIG. 8 is a perspective view of an air purifier according to another embodiment of the present disclosure.

In another embodiment, as shown in FIG. 8, the air purifier further includes a top housing 801. The top housing 801 is connected to the housing 102 to form an external casing and a cavity of the air purifier. The cavity is used to store parts of the air purifier. The cavity may also be used to store air. In the embodiment, the through hole 103 is an inlet of the air purifier. Air passes through the through hole 103 to enter the cavity. The foregoing structure can simplify the structure of the air purifier and reduce processing costs.

In another embodiment, the air purifier further includes a fan, a negative ion generator, a filter, and an ozone module. The fan can suck air that enters the air purifier through the inlet 602 to the outlet 603, to ensure the circulation of air in the air purifier. The filter can remove impurities from air. The negative ion generator can generate negative ions in purified air. Dust in the air can be adsorbed by negative ions and deposited, to purify the air. The ozone module can disinfect and sterilize the air again, to further clean the air.

During the use of the air purifier, an air flow from the inlet 602 to the outlet 603 can be formed by the air entering the air purifier under the action of the fan. The air flows into the inlet 602 and sequentially passes through the filter, the irradiation area of the ultraviolet lamp 604, the negative ion generator, and the ozone module. The purified air then flows out of the outlet 603 of the air purifier, so that smoke and dust in surrounding air can be effectively removed for purification.

The embodiments of the present disclosure are described above in detail with reference to the accompanying drawings, but the present disclosure is not limited to the above embodiments. Within the scope of knowledge possessed by a person of ordinary skill in the art, various modifications can be further made without departing from the purpose of the present disclosure. In addition, the embodiments of the present disclosure and features in the embodiments may be combined with each other without a conflict.

What is claimed is:
1. A light blocking apparatus, comprising:
a housing provided with a through hole; and
a light blocking member, a gap or an angle being provided between the light blocking member and the housing, and an orthographic projection of the light blocking member toward the housing covering the through hole, wherein
the light blocking apparatus comprises a plurality of first connecting members and a plurality of light blocking members, the housing is provided with a plurality of through holes, each of the plurality of first connecting members is connected directly to a respective one of the plurality of light blocking members, and each of the plurality of first connecting members are connected directly to the housing, and wherein the light blocking apparatus further comprises a second connecting member, each of the plurality of light blocking members corresponds to a respective one of the plurality of through holes, one end of the second connecting member is connected to all of the plurality of light blocking members, and the other end of the second connecting member is connected to the housing.

2. The light blocking apparatus of claim 1, wherein a portion of an edge of each of the plurality of light blocking members is connected to the housing.

3. The light blocking apparatus of claim 1, wherein the housing comprises an accommodating cavity with a cavity wall, each of the plurality of through holes is located in the cavity wall, and each of the plurality of light blocking members is located inside or outside the accommodating cavity.

4. An air purifier, comprising the light blocking apparatus of claim 1.

5. The air purifier of claim 4, wherein the air purifier further comprises a top housing which is connected to the housing to form a casing of the air purifier.

6. The air purifier of claim 4, wherein the air purifier comprises a casing, and the light blocking apparatus is located inside the casing.

7. An air purifier, comprising the light blocking apparatus of claim 1, and further comprising a casing and an ultraviolet lamp, wherein the light blocking apparatus is located inside the casing, and the ultraviolet lamp is located in the accommodating cavity.

\* \* \* \* \*